(12) United States Patent
Wadke et al.

(10) Patent No.: US 10,047,655 B2
(45) Date of Patent: Aug. 14, 2018

(54) INTEGRATED SENSOR WATER SHIELD

(71) Applicant: Cummins Emission Solutions, Inc., Columbus, IN (US)

(72) Inventors: Aashish Wadke, Columbus, IN (US); Snehal Khisty, Greenwood, IN (US); Jim Alonzo, Verona, WI (US); Elizabeth Balke, St. Paul, MN (US)

(73) Assignee: CUMMINS EMISSION SOLUTIONS, INC., Columbus, IN (US)

( * ) Notice: Subject to any disclaimer, the term of this patent is extended or adjusted under 35 U.S.C. 154(b) by 0 days.

(21) Appl. No.: 15/101,230

(22) PCT Filed: Dec. 9, 2014

(86) PCT No.: PCT/US2014/069292
§ 371 (c)(1),
(2) Date: Jun. 2, 2016

(87) PCT Pub. No.: WO2015/094812
PCT Pub. Date: Jun. 25, 2015

(65) Prior Publication Data
US 2016/0305297 A1 Oct. 20, 2016

Related U.S. Application Data

(60) Provisional application No. 61/917,688, filed on Dec. 18, 2013.

(51) Int. Cl.
*F01N 9/00* (2006.01)
*F01N 3/20* (2006.01)
(Continued)

(52) U.S. Cl.
CPC ............... *F01N 3/208* (2013.01); *F01N 9/00* (2013.01); *G01D 11/245* (2013.01);
(Continued)

(58) Field of Classification Search
CPC ........ F01N 9/00; F01N 3/208; G01M 15/102; G01D 11/245
See application file for complete search history.

(56) References Cited

U.S. PATENT DOCUMENTS 4,011,654 A * 3/1977 Beaudoin ............... G01N 27/12
264/614
4,148,211 A * 4/1979 Sawa ................... F02D 41/1439
204/409

(Continued)

OTHER PUBLICATIONS

International Search Report and Written Opinion for PCT/US2014/069292, dated Mar. 2, 2015, 12 Pages.

*Primary Examiner* — Harshad R Patel
*Assistant Examiner* — Jamel Williams
(74) *Attorney, Agent, or Firm* — Foley & Lardner LLP

(57) ABSTRACT

A sensor probe for an exhaust system including a sensor body, a sensor cup, and a fluid shield. The sensor body defines a conduit and having a plurality of apertures formed through a sidewall of the sensor body. The sensor cup is coupled to an end of the conduit of the sensor body and is in fluid communication with the conduit. The sensor cup includes an outlet formed therein. The fluid shield may be integrally coupled to the sensor cup and positioned relative to the outlet formed in the sensor cup such that the fluid shield deflects fluid away from the outlet.

20 Claims, 6 Drawing Sheets

(51) Int. Cl.
*G01N 33/00* (2006.01)
*G01D 11/24* (2006.01)
*G01M 15/10* (2006.01)
*G01N 27/407* (2006.01)

(52) U.S. Cl.
CPC ........ G01M 15/102 (2013.01); G01N 33/004 (2013.01); G01N 33/0009 (2013.01); G01N 33/0037 (2013.01); *F01N 2560/02* (2013.01); *F01N 2560/026* (2013.01); *F01N 2900/0416* (2013.01); *G01N 27/407* (2013.01); *Y02A 50/245* (2018.01); *Y02T 10/24* (2013.01); *Y02T 10/47* (2013.01)

(56) References Cited

U.S. PATENT DOCUMENTS

| | | | |
|---|---|---|---|
| 4,208,266 A | 6/1980 | Auman et al. | |
| 6,898,961 B2 | 5/2005 | Yamada et al. | |
| 2002/0018305 A1 | 2/2002 | Kohno | |
| 2005/0252177 A1* | 11/2005 | Ishikawa | B01D 39/2093 55/282.3 |
| 2008/0206107 A1* | 8/2008 | Thanigachalam | G01N 27/12 422/94 |
| 2012/0018305 A1* | 1/2012 | Yoshikawa | G01N 27/4077 204/431 |
| 2013/0171035 A1* | 7/2013 | Wikaryasz | B01D 53/94 422/170 |

\* cited by examiner

INTEGRATED SENSOR WATER SHIELD

CROSS-REFERENCE TO RELATED APPLICATIONS

The present application is a U.S. national stage application claiming the benefit of International Application No. PCT/US2014/069292, filed on Dec. 9, 2014, which claims the benefit of priority from U.S. Provisional Patent Application No. 61/917,688, filed on Dec. 18, 2013. Both applications are hereby incorporated by reference in their entirety for all purposes.

TECHNICAL FIELD

The present application relates generally to the field of sensor systems for exhaust systems. More specifically, the present application relates to sensor probes for an exhaust system.

BACKGROUND

For internal combustion engines, such as diesel or natural gas engines, nitrogen oxide ($NO_x$) compounds may be emitted in the exhaust of a vehicle. To reduce $NO_x$ emissions, a selective catalytic reduction (SCR) process may be implemented to convert the $NO_x$ compounds into more neutral compounds, such as diatomic nitrogen, water, or carbon dioxide, with the aid of a catalyst and a reductant. The catalyst may be included in a catalyst chamber of an exhaust system. A reductant, such as anhydrous ammonia, aqueous ammonia, or urea is typically introduced into the exhaust gas flow prior to the catalyst chamber. To introduce the reductant into the exhaust gas flow for the SCR process, an SCR system may dose or otherwise introduce the reductant through a dosing module that vaporizes or sprays the reductant into an exhaust pipe of the exhaust system upstream of the catalyst chamber.

SUMMARY

Implementations described herein relate to sensor probes that include a fluid shield for shielding an outlet of the sensor probe from fluid or debris.

One implementation relates to a sensor probe for an exhaust system that includes a sensor body that defines at least one conduit and has several apertures formed through a sidewall of the sensor body. The sensor probe also includes a sensor cup that is coupled to an end of the at least one conduit of the sensor body and is in fluid communication with the at least one conduit. The sensor cup includes an outlet formed in the sensor cup. The sensor probe further includes a fluid shield that is integrally coupled to the sensor cup and is positioned relative to the outlet formed in the sensor cup such that the fluid shield deflects fluid away from the outlet.

Another implementation relates to a method for constructing a sensor probe for an exhaust system. The method includes constructing a sensor body that includes at least one conduit and several apertures formed in a sidewall of the sensor body. The method also includes welding the sensor body to a sensor cup. The sensor cup is in fluid communication with the at least one conduit and includes an outlet formed in the sensor cup. The method further includes welding a fluid shield to a portion of the sensor cup. The fluid shield is positioned relative to the outlet formed in the sensor cup such that the fluid shield deflects fluid away from the outlet.

Yet another implementation relates to a sensor probe for an exhaust system. The sensor probe includes a sensor cup having an outlet formed in the sensor cup. The sensor probe also includes a fluid shield having a curved upper portion extending upwardly and outwardly at an angle relative to the sensor cup. The fluid shield is coupled to the sensor cup, and a first end of the curved upper portion extends beyond a first edge of the outlet and a second end of the curved upper portion extends beyond a second edge of the outlet with the second edge being opposite the first edge. The curved upper portion of the fluid shield forms an overhang to substantially deflect fluid away from the outlet while permitting fluid to exit the outlet.

BRIEF DESCRIPTION OF THE DRAWINGS

The details of one or more implementations are set forth in the accompanying drawings and the description below. Other features, aspects, and advantages of the disclosure will become apparent from the description, the drawings, and the claims, in which:

Figure 1:
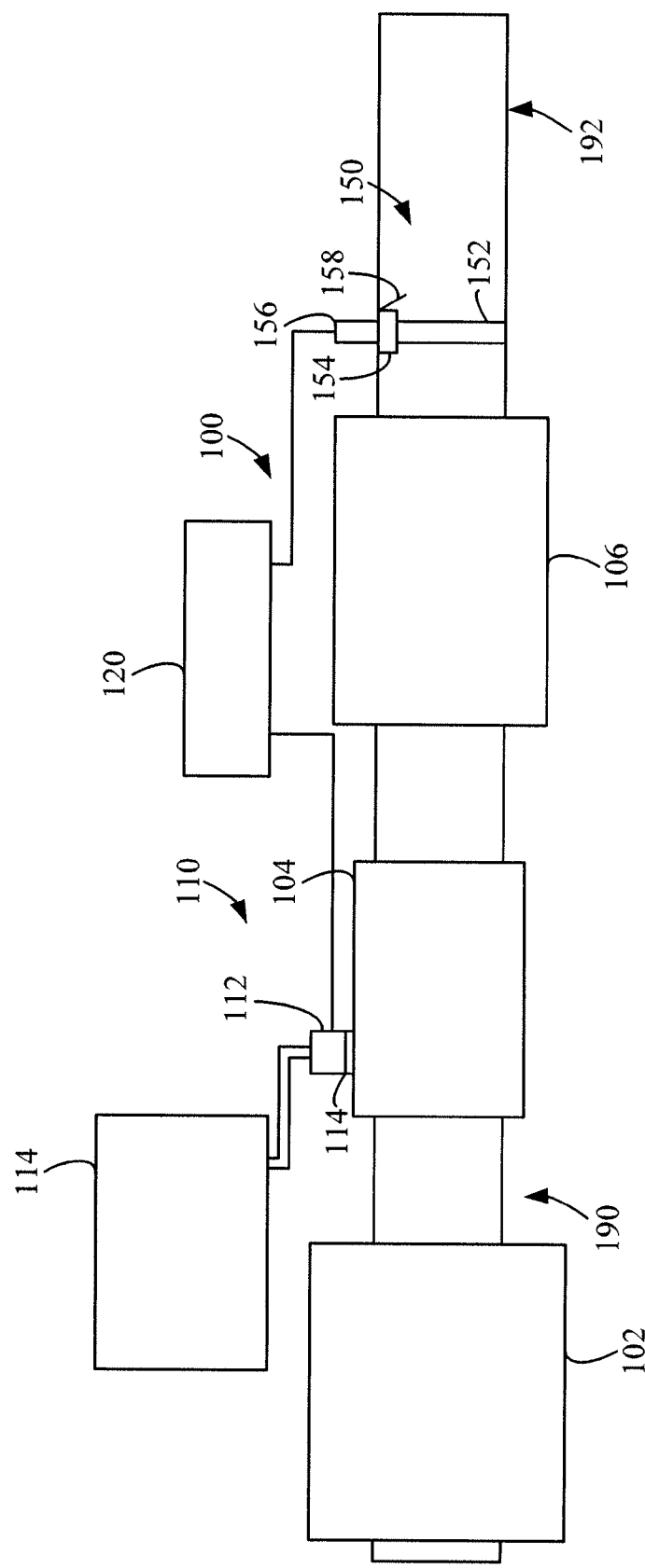
FIG. 1 is a block schematic diagram of an example selective catalytic reduction system having an example reductant delivery system for an exhaust system.

It will be recognized that some or all of the figures are schematic representations for purposes of illustration. The figures are provided for the purpose of illustrating one or more implementations with the explicit understanding that they will not be used to limit the scope or the meaning of the claims.

DETAILED DESCRIPTION

Following below are more detailed descriptions of various concepts related to, and implementations of, methods, apparatuses, and systems for providing a fluid shield for a sensor probe positioned in an exhaust of a vehicle. The various concepts introduced above and discussed in greater detail below may be implemented in any of numerous ways, as the described concepts are not limited to any particular manner of implementation. Examples of specific implementations and applications are provided primarily for illustrative purposes.

I. Overview

In some vehicles, such as semi-trailer trucks or tractors, an outlet of an exhaust system is vertical or substantially vertical relative to the vehicle. Thus, an end opening of the exhaust may be open and exposed to the environment, thereby potentially exposing any components within the exhaust system to any environmental conditions. In some exhaust systems, a sensor module may be located downstream of an SCR catalyst to detect one or more emissions in the exhaust flow after the SCR catalyst. For example, a $NO_x$ sensor, a CO sensor, and/or a particulate matter sensor may be positioned downstream of the SCR catalyst to detect $NO_x$, CO, and/or particulate matter within the exhaust gas exiting the exhaust of the vehicle. Such emission sensors may be useful to provide feedback to a controller to modify an operating parameter of the aftertreatment system of the vehicle. For example, a $NO_x$ sensor may be utilized to detect the amount of $NO_x$ exiting the vehicle exhaust system and, if the $NO_x$ detected is too high or too low, the controller may modify an amount of reductant delivered by a dosing module. A CO and/or a particulate matter sensor may also be utilized.

In some implementations, the sensor probe may be located in the vertical portion of the exhaust system of the vehicle. Thus, the sensor probe may be, at least partially, exposed to the environmental conditions the outlet or end opening of the exhaust system is exposed to, such as rain, snow, hail, etc. For example, fluid may fall into the exhaust outlet and, in some instances, enter the sensor probe, thereby potentially damaging or causing the sensor of the sensor probe to fail. In other instances, fluid may enter the sensor probe in other manners, such as during cleaning of the vehicle. Such fluid intrusion failure modes may be reduced if the fluid is prevented or substantially deflected away from the sensor probe and/or the sensor. In some implementations, a fluid shield may be provided with the sensor probe such that the fluid shield deflects fluid away from the sensor of the sensor probe, thereby reducing and/or potentially eliminating incidents of fluid intrusion failure modes. In addition, such a fluid shield and sensor probe may be constructed such that the exhaust gases that are sensed by the sensor of the sensor probe are released by into the exhaust gas to prevent gaseous build-up at the sensor. For example, a mesh covering may be provided in a sensor cup of the sensor probe such that exhaust gases within the sensor cup may be released back into the exhaust system. In such a construction, the fluid shield may be constructed with the shield probe such that the fluid shield deflects fluid from entering the mesh covering. The construction and positioning of the fluid shield may be such that the fluid shield does not substantially affect the function of the sensor probe so the sensor probe may continue to monitor the emission reading with the same accuracy as if no shield is provided.

II. Overview of Aftertreatment System

FIG. 1 depicts an aftertreatment system 100 having an example reductant delivery system 110 for an exhaust system 190. The aftertreatment system 100 includes a diesel particulate filter (DPF) 102, the reductant delivery system 110, a decomposition chamber or reactor 104, a SCR catalyst 106, and a sensor probe 150.

The DPF 102 is configured to remove particulate matter, such as soot, from exhaust gas flowing (indicated by arrow 192) in the exhaust system 190. The DPF 102 includes an inlet, where the exhaust gas is received, and an outlet, where the exhaust gas exits after having particulate matter substantially filtered from the exhaust gas and/or converting the particulate matter into carbon dioxide.

The decomposition chamber 104 is configured to convert a reductant, such as urea, aqueous ammonia, or diesel exhaust fluid (DEF), into ammonia. The decomposition chamber 104 includes a reductant delivery system 110 having a dosing module 112 configured to dose the reductant into the decomposition chamber 104. In some implementations, the urea, aqueous ammonia, DEF is injected upstream of the SCR catalyst 106. The reductant droplets then undergo the processes of evaporation, thermolysis, and hydrolysis to form gaseous ammonia within the exhaust system 190. The decomposition chamber 104 includes an inlet in fluid communication with the DPF 102 to receive the exhaust gas containing $NO_x$ emissions and an outlet for the exhaust gas, $NO_x$ emissions, ammonia, and/or remaining reductant to flow to the SCR catalyst 106.

The decomposition chamber 104 includes the dosing module 112 mounted to the decomposition chamber 104 such that the dosing module 112 may dose a reductant, such as urea, aqueous ammonia, or DEF, into the exhaust gases flowing in the exhaust system 190. The dosing module 112 may each include an insulator 114 interposed between a portion of the dosing module 112 and the portion of the decomposition chamber 104 to which the dosing module 112 is mounted. The dosing module 112 is fluidly coupled to one or more reductant sources 116. In some implementations, a pump (not shown) may be used to pressurize the reductant source 116 for delivery to the dosing module 112.

The dosing module 112 is also electrically or communicatively coupled to a controller 120. The controller 120 is configured to control the dosing module 112 to dose reductant into the decomposition chamber 104. The controller 120 may include a microprocessor, an application-specific integrated circuit (ASIC), a field-programmable gate array (FPGA), etc., or combinations thereof. The controller 120 may include memory which may include, but is not limited to, electronic, optical, magnetic, or any other storage or transmission device capable of providing a processor, ASIC, FPGA, etc. with program instructions. The memory may include a memory chip, Electrically Erasable Programmable Read-Only Memory (EEPROM), erasable programmable read only memory (EPROM), flash memory, or any other suitable memory from which the controller 120 can read instructions. The instructions may include code from any suitable programming language.

The SCR catalyst 106 is configured to assist in the reduction of $NO_x$ emissions by accelerating a $NO_x$ reduction process between the ammonia and the $NO_x$ of the exhaust gas into diatomic nitrogen, water, and/or carbon dioxide. The SCR catalyst 106 includes inlet in fluid communication with the decomposition chamber 104 from which exhaust gas and reductant is received and an outlet in fluid communication with an end 192 of the exhaust system 190.

The exhaust system 190 may further include a diesel oxidation catalyst (DOC) in fluid communication with the exhaust system 190 (e.g., downstream of the SCR catalyst 106 or upstream of the DPF 102) to oxidize hydrocarbons and carbon monoxide in the exhaust gas.

A sensor probe 150 is located downstream of the SCR catalyst 106 within an end 192 of the exhaust system 192. The sensor probe 150 may include a sensor body 152 configured with receive a portion of the exhaust gases flowing within the exhaust system 190, as will be described in greater detail in reference to FIGS. 2-3. The sensor probe 150 further includes a sensor cup 154 having an end in fluid communication with the sensor body 152 and having a portion of a sensor 156 extending into the sensor cup 154. The sensor cup 154 is configured to aggregate the portion of the exhaust gas received in the sensor body 152 such that the sensor 156 extending within the sensor cup 154 may detect the amount of the emission, such as $NO_x$, CO, and/or particulate matter, within the portion of the exhaust gas. In some implementations, the sensor cup 154 includes an outlet from which the portion of the exhaust gas within the sensor cup 154 may flow back out into the end 192 of the exhaust system 190. The sensor probe 150 further includes a fluid shield 158 extending from the sensor cup 154 to shield a rear portion of the sensor cup out of which the exhaust gas flows from the outlet of the sensor cup 154. The sensor probe 150 and fluid shield 158 will be described in greater detail herein.

III. Example Sensor Probe

Figure 2:
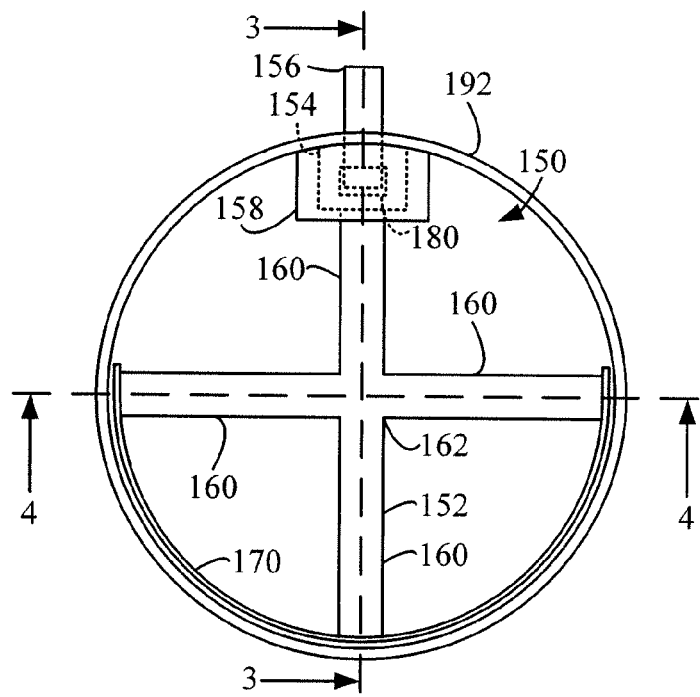
FIG. 2 is a top plan diagram of an example sensor probe having an integrated fluid shield.
Figure 3:
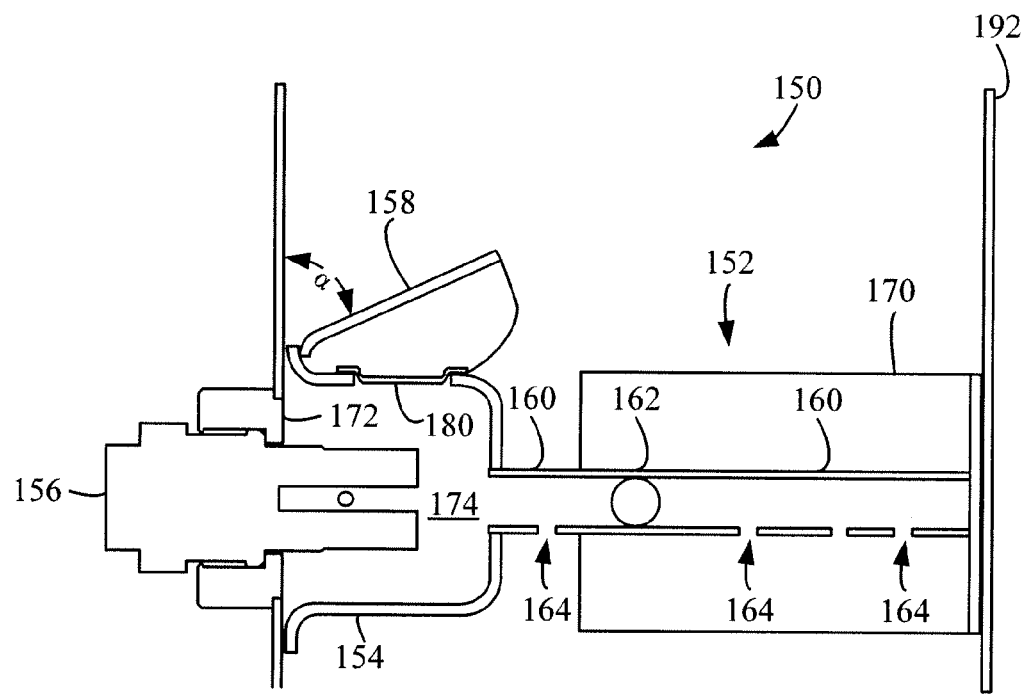
FIG. 3 is a side cross-sectional view of the example sensor probe of FIG. 2 taken along line 3-3 in FIG. 2.
Figure 4:
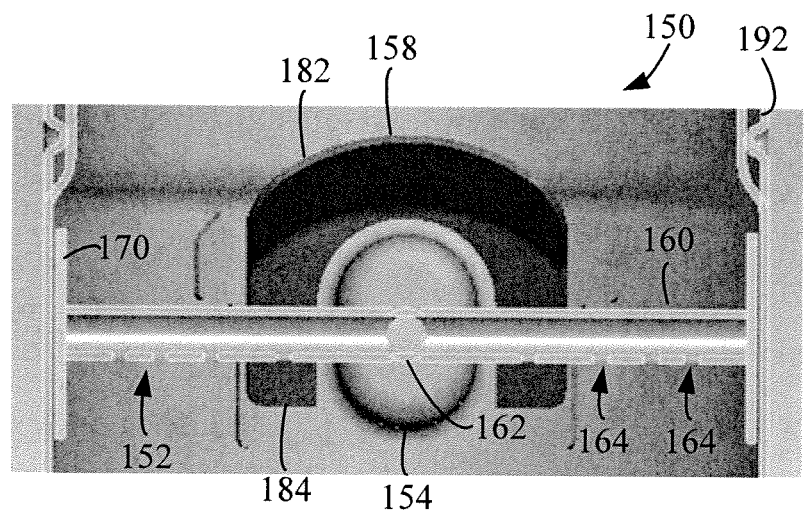
FIG. 4 is a front cross-sectional view of the sensor probe of FIG. 2 taken along line 4-4 in FIG. 2.
Figure 5:
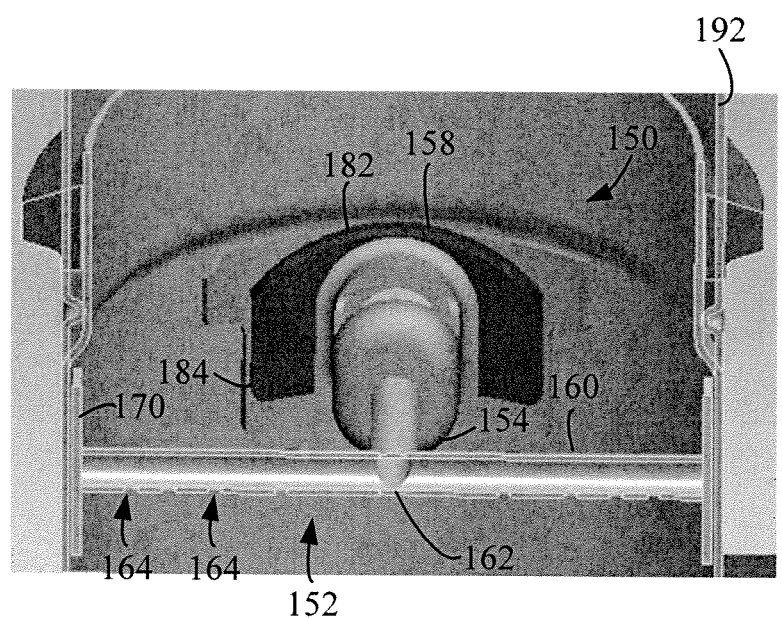
FIG. 5 is a perspective view of the front cross-sectional view of FIG. 4.
Figure 6:
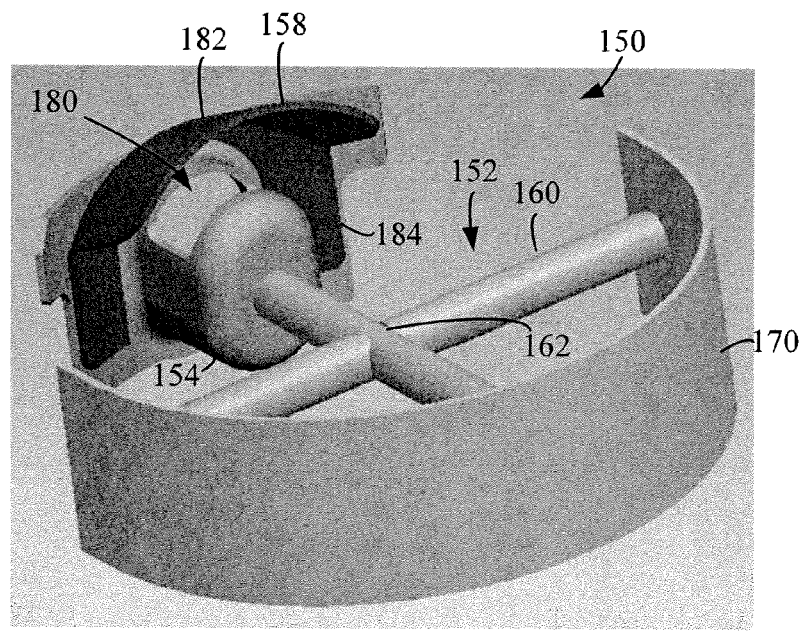
FIG. 6 is a perspective view of the sensor probe of FIG. 2.
Figure 7:
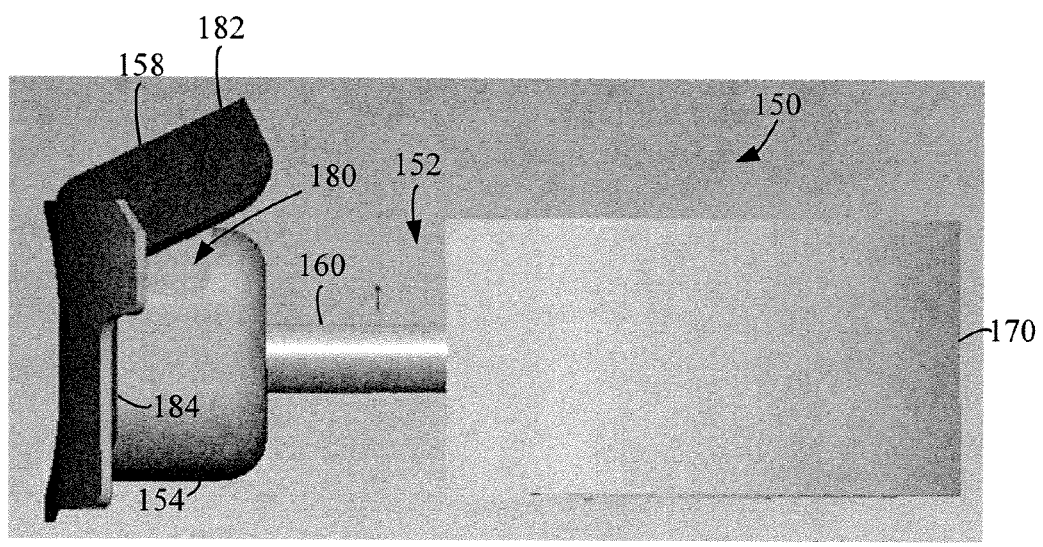
FIG. 7 is a side elevational view of the sensor probe of FIG. 2.
Figure 8:
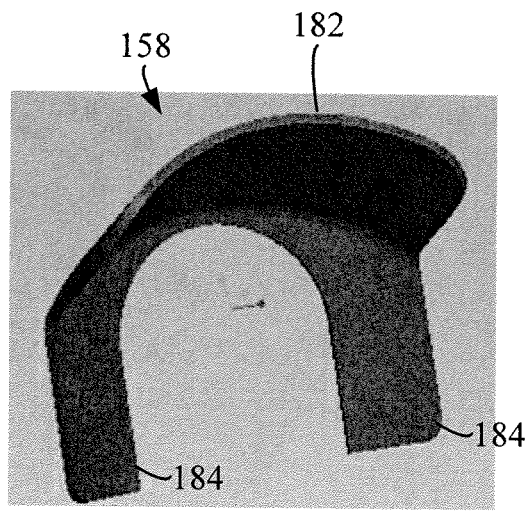
FIG. 8 depicts a perspective view of a fluid shield of the sensor probe of FIG. 2.
Figure 9:
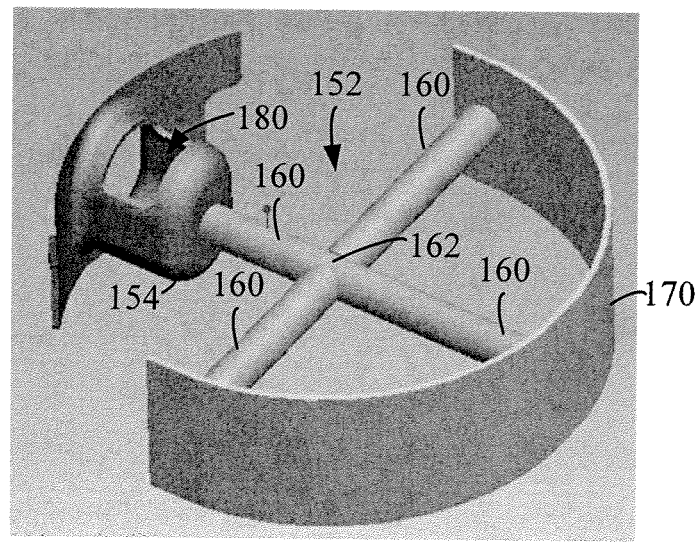
FIG. 9 depicts a perspective view of a sensor body, a sensor cup, and an arcuate positioning member of the sensor probe of FIG. 2 and omitting the fluid shield.

FIGS. 2-9 depict the sensor probe 150 and components thereof in greater detail. FIG. 2 depicts a top plan view of the sensor probe 150 positioned within the end 192 of the exhaust system 190. FIG. 3 depicts a side cross-sectional view of the sensor probe 150 of FIG. 2 taken along line 3-3 in FIG. 2. FIG. 4 depicts a front cross-sectional view of the sensor probe 150 of FIG. 2 taken along line 4-4 in FIG. 2. FIG. 5 is a perspective view of the front cross-sectional view of FIG. 4. FIG. 6 is a perspective view of the sensor probe 150 of FIG. 2. FIG. 7 is a side elevational view of the sensor probe 150 of FIG. 2. FIG. 8 depicts a perspective view of a fluid shield 158 of the sensor probe 150 of FIG. 2. FIG. 9 depicts a perspective view of the sensor body 152, the sensor cup 154, and the arcuate positioning member 170 of the sensor probe 150 without the fluid shield 158.

Referring generally to FIGS. 2-9, the sensor probe includes a sensor body 152 having a plurality of legs 160 and an arcuate positioning member 170. In the example shown, the sensor body 152 includes four legs 160 intersecting at a central intersection 162. In some implementations, two legs 160 may be used. In other implementations, three legs 160 may be used. In still further implementations, more than four legs 160 may be used. The legs 160 may be equally spaced relative to adjacent legs 160, the legs 160 may be asymmetrically spaced, and/or otherwise configured. Each leg 160 defines a conduit therein.

A base leg 160 is coupled to and in fluid communication with the sensor cup 154 (shown in phantom in FIG. 2) at a first end and terminating at a second end at the central intersection 162. In the present example, the three other legs 160 are coupled to and in fluid communication with the base leg 160 via the central intersection 162 at a respective second end of each leg 160 and extend from the central intersection 162 outwardly toward the arcuate positioning member 170. Each respective first end of the other legs 160 are coupled to and are fluidly sealed to the arcuate positioning member 170.

The arcuate positioning member 170 of the present example is a substantially hemicylindrical member configured to fit within the end 192 of the exhaust system 190. In some implementations, the arcuate positioning member 170 may be sized such that the arcuate positioning member 170 forms an interference fit within the end 192 of the exhaust system 190. In other implementations, the arcuate positioning member 170 may not form an interference fit within the exhaust system 190, and the arcuate positioning member 170 may be mechanically coupled to or mounted within the end 192 of the exhaust system 190. For example, the arcuate positioning member 170 may substantially align the sensor body 152 within the end 192 of the exhaust system 190 and the arcuate positioning member 170 may be welded, bolted, or otherwise mechanically coupled to the exhaust system 190. In still further implementations, the arcuate positioning member 170 may be a substantially cylindrical member and may be positioned between and coupled to portions of the exhaust system 190 (e.g., a cylindrical member to which an end of the exhaust system from the SCR catalyst 106 may be coupled to a first end of the cylindrical member and to which the end 192 of the exhaust system 190, such as a vertical stack exhaust pipe, may be coupled to a second end of the cylindrical member).

The legs 160 each include one or more inlet apertures 164, shown in FIG. 3, formed through a sidewall of each leg 160 into which a portion of the exhaust gas flowing in the exhaust system 190 may be received into the conduit defined by each leg 160. The exhaust gas is transported within the other legs 160 to the central intersection 162 and then through the base leg 160, along with exhaust gas received by any inlet apertures 164 of the base leg 160, to the sensor cup 154.

The sensor cup 154 includes an opening 172 through which a portion of the sensor 156 is received, opposite the base leg 160. The sensor 156 may include a $NO_x$ sensor, a CO sensor, a particulate matter sensor, or any other emissions sensor. In some implementations, several sensors may have a sensing portion positioned within an interior volume 174 of the sensor cup 154 to detect an amount of a corresponding emission within the exhaust gas (such as a $NO_x$ sensor and a CO sensor) within the volume 174 of the sensor cup 154.

The sensor cup 154 further includes an outlet 180 (shown in phantom in FIG. 2) out of which exhaust gas within the sensor cup 154 may flow back into the exhaust system 190. In the present example, the outlet 180 may include a mesh covering, such as a metal mesh. In other implementations, the outlet 180 may simply be an open aperture. In still further implementations, the outlet 180 may include grating, a grille, or other structure through which a fluid may flow. In some implementations the outlet 180 having a mesh covering may be integrally with the sensor cup 154 (e.g., formed when the sensor cup 154 is formed, such as through injection molding, or machined into the sensor cup 154, such as drilling a plurality of holes within the sensor cup 154). In other implementations, the outlet 180 have the mesh covering may be formed separately from the sensor cup 154 and coupled to an aperture formed in the sensor cup 154 (e.g., via welding).

A fluid shield 158 is integral (e.g., via welding or integral formation) with the sensor cup 154 and includes a curved upper portion 182 (shown best in FIG. 4) that extends upwardly relative to the sensor cup 154 and outwardly toward the central intersection 162 such that the fluid shield 180, when the exhaust system 190 within which the sensor probe 150 is position is in a substantially vertical orientation, forms an overhang over the sensor cup 154 and the outlet 180 of the sensor cup 154. In some implementations, the fluid shield 158 is positioned such that the fluid shield 158 forms an angle $\alpha$ relative to a wall of the end 192 of the exhaust system 190. The angle $\alpha$ may be an angle from about 30 degrees, inclusive, to about 90 degrees, inclusive. In some implementations, the angle $\alpha$ may be about 65 degrees. In other implementations, the angle $\alpha$ may be 45 degrees. In other implementations, the angle $\alpha$ may be about 60 degrees.

Referring generally to FIGS. 4-8, the fluid shield 158 of the present example has a curved upper portion 182 and a pair of curved side portions 184 that extend about the sensor cup 154. The curved upper portion 182 forms an overhang over the sensor cup 154 such that fluids (e.g., water, water mixtures, oil, etc.) are deflected away from the sensor cup 154 when the fluid is moving in a direction substantially perpendicular to a plane in which the sensor probe 150 lies. In some implementations, the curved side portions 184 may be welded or otherwise integrally coupled to the sensor cup 154 and/or to another portion of the sensor probe 150.

Figure 10:
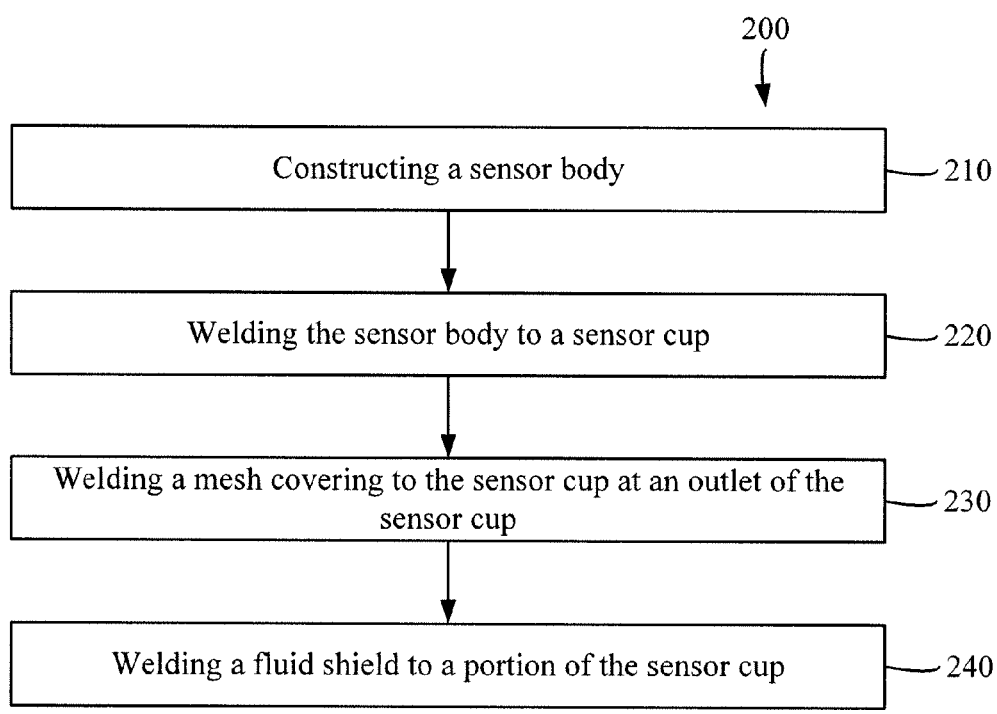
FIG. 10 is a flow diagram depicting an example process for constructing a sensor probe having an integrated fluid shield.

FIG. 10 depicts an example process 200 for manufacturing a sensor probe 150 having an integral fluid shield 158. The process may include constructing a sensor body 150 at 210. The process 200 may further include welding the sensor body 152 to a sensor cup 154 at 220. The process 200 further includes welding a mesh covering to the sensor cup 154 at an outlet 180 of the sensor cup 154 at 230. The process 200 still further includes welding a fluid shield 158 to a portion of the sensor cup 154 at 240. In some implementations, the sensor probe 150 is positioned within a substantially vertical portion of an exhaust system 190. The sensor probe 150 may be welded into the exhaust system 190 and/or otherwise coupled to the exhaust system 190. In some implementations, a sensor 156 is inserted through an opening 172 such that a portion of the sensor 156 extends into a volume 174 of the sensor cup 154.

The term "controller" encompasses all kinds of apparatus, devices, and machines for processing data, including by way of example a programmable processor, a computer, a system on a chip, or multiple ones, a portion of a programmed processor, or combinations of the foregoing. The apparatus can include special purpose logic circuitry, e.g., an FPGA or an ASIC. The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as distributed computing and grid computing infrastructures.

A computer program (also known as a program, software, software application, script, or code) can be written in any form of programming language, including compiled or interpreted languages, declarative or procedural languages, and it can be deployed in any form, including as a standalone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code).

While this specification contains many specific implementation details, these should not be construed as limitations on the scope of what may be claimed, but rather as descriptions of features specific to particular implementations. Certain features described in this specification in the context of separate implementations can also be implemented in combination in a single implementation. Conversely, various features described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, the separation of various system components in the implementations described above should not be understood as requiring such separation in all implementations, and it should be understood that the described components and systems can generally be integrated in a single product or packaged into multiple products embodied on tangible media.

As utilized herein, the terms "approximately," "about," "substantially", and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the invention as recited in the appended claims. Additionally, it is noted that limitations in the claims should not be interpreted as constituting "means plus function" limitations under the United States patent laws in the event that the term "means" is not used therein.

The terms "coupled," "connected," and the like as used herein mean the joining of two components directly or indirectly to one another. Such joining may be stationary (e.g., permanent) or moveable (e.g., removable or releasable). Such joining may be achieved with the two components or the two components and any additional intermediate components being integrally formed as a single unitary body with one another or with the two components or the two components and any additional intermediate components being attached to one another.

The terms "fluidly coupled," "in fluid communication," and the like as used herein mean the two components or objects have a pathway formed between the two components or objects in which a fluid, such as water, air, gaseous reductant, gaseous ammonia, etc., may flow, either with or without intervening components or objects. Examples of fluid couplings or configurations for enabling fluid communication may include piping, channels, or any other suitable components for enabling the flow of a fluid from one component or object to another.

It is important to note that the construction and arrangement of the system shown in the various exemplary implementations is illustrative only and not restrictive in character. All changes and modifications that come within the spirit and/or scope of the described implementations are desired to be protected. It should be understood that some features may not be necessary and implementations lacking the various features may be contemplated as within the scope of the application, the scope being defined by the claims that follow. In reading the claims, it is intended that when words such as "a," "an," "at least one," or "at least one portion" are used there is no intention to limit the claim to only one item unless specifically stated to the contrary in the claim. When the language "at least a portion" and/or "a portion" is used the item can include a portion and/or the entire item unless specifically stated to the contrary.

What is claimed is:

1. A sensor probe for an exhaust system, comprising:
   a sensor body defining at least one conduit and having a plurality of apertures formed through a sidewall of the sensor body;
   a sensor cup coupled to an end of the at least one conduit of the sensor body and in fluid communication with the at least one conduit, the sensor cup having an outlet formed in a sidewall of the sensor cup out of which gas within the sensor cup flows back into the exhaust system; and
   a fluid shield integrally coupled to the sensor cup and positioned relative to the outlet formed in the sensor cup such that the fluid shield deflects fluid away from the outlet when the fluid is moving in a direction perpendicular to a plane in which the sensor probe lies.

2. The sensor probe of claim 1, wherein the fluid shield includes a curved upper portion disposed at an angle of between about 30 degrees and about 90 degrees relative to a wall of the exhaust system.

3. The sensor probe of claim 1, wherein the fluid shield includes a curved upper portion disposed at an angle of about 65 degrees relative to a wall of the exhaust system.

4. The sensor probe of claim 1, further comprising a wire mesh covering the outlet.

5. The sensor probe of claim 1, further comprising a positioning member coupled to a second end of the at least one conduit, the positioning member configured to position the sensor probe within an exhaust system.

6. The sensor probe of claim 5, wherein the positioning member is an arcuate positioning member.

7. The sensor probe of claim 6, wherein the sensor body further defines a second conduit coupled to the at least one conduit, the second conduit in fluid communication with the at least one conduit and the sensor cup.

8. The sensor probe of claim 7, wherein the second conduit is substantially perpendicular to at least one conduit are perpendicular.

9. The sensor probe of claim 8, wherein a third end of the second conduit is coupled to the arcuate positioning member.

10. The sensor probe of claim 1, wherein the sensor probe is positioned within a substantially vertical portion of the exhaust system.

11. A method for constructing a sensor probe for an exhaust system, the method comprising:
    constructing a sensor body, the sensor body including at least one conduit and a plurality of apertures formed in a sidewall of the sensor body;
    welding the sensor body to a sensor cup, the sensor cup in fluid communication with the at least one conduit and including an outlet formed in a sidewall of the sensor cup out of which gas within the sensor cup flows back into the exhaust system; and
    welding a fluid shield to a portion of the sensor cup, the fluid shield positioned relative to the outlet formed in the sensor cup such that the fluid shield deflects fluid away from the outlet when the fluid is moving in a direction perpendicular to a plane in which the sensor probe lies.

12. The method of claim 11 further comprising welding a wire mesh over the outlet of the sensor cup.

13. The method of claim 11 further comprising positioning the sensor probe within a substantially vertical portion of the exhaust system.

14. The method of claim 13, wherein the fluid shield includes a curved upper portion disposed at an angle of about 65 degrees relative to the substantially vertical portion of the exhaust system.

15. The method of claim 11 further comprising inserting a sensor through an opening of the sensor cup, the opening substantially opposite the at least one conduit.

16. A sensor probe for an exhaust system, comprising:
    a sensor cup having an outlet formed in a sidewall of the sensor cup out of which gas within the sensor cup flows back into the exhaust system; and
    a fluid shield having a curved upper portion extending upwardly and outwardly at an angle relative to the sensor cup, wherein the fluid shield is coupled to the sensor cup, wherein a first end of the curved upper portion extends beyond a first edge of the outlet and a second end of the curved upper portion extends beyond a second edge of the outlet, wherein the second edge is opposite the first edge, wherein the curved upper portion of the fluid shield forms an overhang to substantially deflect fluid away from the outlet when the fluid is moving in a direction perpendicular to a plane in which the sensor probe lies and permits gas to exit the outlet.

17. The sensor probe of claim 16, wherein the curved upper portion deflects fluid from a first direction away from the outlet relative to the sensor cup while permitting gas to exit the outlet from a second direction relative to the sensor cup, wherein the first direction is opposite the second direction.

18. The sensor probe of claim 16 further comprising a sensor body defining at least one conduit and having a plurality of apertures formed through a sidewall of the sensor body,
    wherein a portion of the sensor cup is coupled to an end of the at least one conduit of the sensor body and in fluid communication with the at least one conduit, wherein fluid flows through the at least one conduit into the sensor body and out through the outlet.

19. The sensor probe of claim 16, wherein the sensor probe is positioned within a substantially vertical portion of the exhaust system, wherein exhaust travelling through the exhaust system travels substantially in the second direction.

20. The sensor probe of claim 16, wherein the curved upper portion is disposed at an angle of between about 30 degrees and about 90 degrees relative to a wall of the exhaust system.

* * * * *